(12) United States Patent
Rahn

(10) Patent No.: US 11,243,173 B2
(45) Date of Patent: Feb. 8, 2022

(54) STONE-BLOCK ANALYSIS DEVICE AND METHODS FOR THE EVALUATION OF STONE BLOCKS

(71) Applicant: R&W INDUSTRIEAUTOMATION GMBH, Hachenburg (DE)

(72) Inventor: Uwe Rahn, Alpenrod (DE)

(73) Assignee: R&W INDUSTRIEAUTOMATION GMBH

(\*) Notice: Subject to any disclaimer, the term of this patent is extended or adjusted under 35 U.S.C. 154(b) by 0 days.

(21) Appl. No.: 16/939,835

(22) Filed: Jul. 27, 2020

(65) Prior Publication Data

US 2021/0025830 A1  Jan. 28, 2021

(30) Foreign Application Priority Data

Jul. 26, 2019 (EP) .................................. 19188508

(51) Int. Cl.
*G01N 21/89* (2006.01)
*G01N 33/38* (2006.01)
(Continued)

(52) U.S. Cl.
CPC ..... *G01N 21/8901* (2013.01); *G01B 11/0608* (2013.01); *G01B 11/0691* (2013.01);
(Continued)

(58) Field of Classification Search
CPC ........... G01N 21/8901; G01N 21/8851; G01N 33/383; G01N 2021/8887; G01B 11/24;
(Continued)

(56) References Cited

U.S. PATENT DOCUMENTS

| 2012/0304763 A1 | 12/2012 | Troxler | ................... G01N 9/00 |
| 2017/0249727 A1 | 8/2017 | Mayumi | ................. G06T 7/001 |

FOREIGN PATENT DOCUMENTS

| DE | 29702402 | 1/1997 | ............... G01N 9/02 |
| EP | 0657260 | 6/1995 | ............ B28B 17/00 |

(Continued)

OTHER PUBLICATIONS

Intent to Grant issued in European Patent Appln. No. 19 188 508.6-1010, dated Aug. 24, 2021, with machine English translation, 13 pages.

(Continued)

*Primary Examiner* — Jamil Ahmed
(74) *Attorney, Agent, or Firm* — Hayes Soloway P.C.

(57) ABSTRACT

Disclosed is a stone-block analysis device and method for the evaluation of stone blocks, in particular, concrete blocks to be arranged on a conveying device for conveying the stone blocks with a conveying surface for the stone blocks to be laid on, which extends into a longitudinal direction and into a transverse direction. The stone-block analysis device has at least one first scanner unit for scanning at least one physical characteristic of the stone blocks, an evaluation device for evaluating a signal output by the scanner unit, a control device, and a display device. The scanner unit is spaced away from the conveying surface in a vertical direction, perpendicular to the longitudinal direction and transverse direction. In addition to the first scanner unit, which is a point scanner, at least one second scanner unit is provided, which is a line scanner, wherein a height of at least one stone block can be detected by both scanner units.

19 Claims, 4 Drawing Sheets

(51) Int. Cl.
    *G01B 11/06*      (2006.01)
    *G01G 11/00*      (2006.01)
    *G01N 21/88*      (2006.01)

(52) U.S. Cl.
    CPC ......... *G01G 11/00* (2013.01); *G01N 21/8851* (2013.01); *G01N 33/383* (2013.01); *G01N 2021/8887* (2013.01)

(58) Field of Classification Search
    CPC .. G01B 11/0608; G01B 11/0691; G01G 11/00
    See application file for complete search history.

(56) References Cited

FOREIGN PATENT DOCUMENTS

| | | | | | |
|---|---|---|---|---|---|
| JP | H02285235 A | * | 11/1990 | ............. | G01N 33/38 |
| JP | H07128029 A | * | 5/1995 | ............. | G01B 11/24 |

OTHER PUBLICATIONS

Official Action issued in European Patent Appln. No. 19 188 508.6-1010, dated May 12, 2021, 9 pgs, with machine English translation.
Official Action issued in European Patent Appln. No. 19 188 508.6-1010, dated Jul. 23, 2021, 9 pgs, with machine English translation.
Search Report issued in European Patent Appln. No. 19 188 508.6-1010, dated Apr. 24, 2020, 13 pgs, with machine English translation.

* cited by examiner

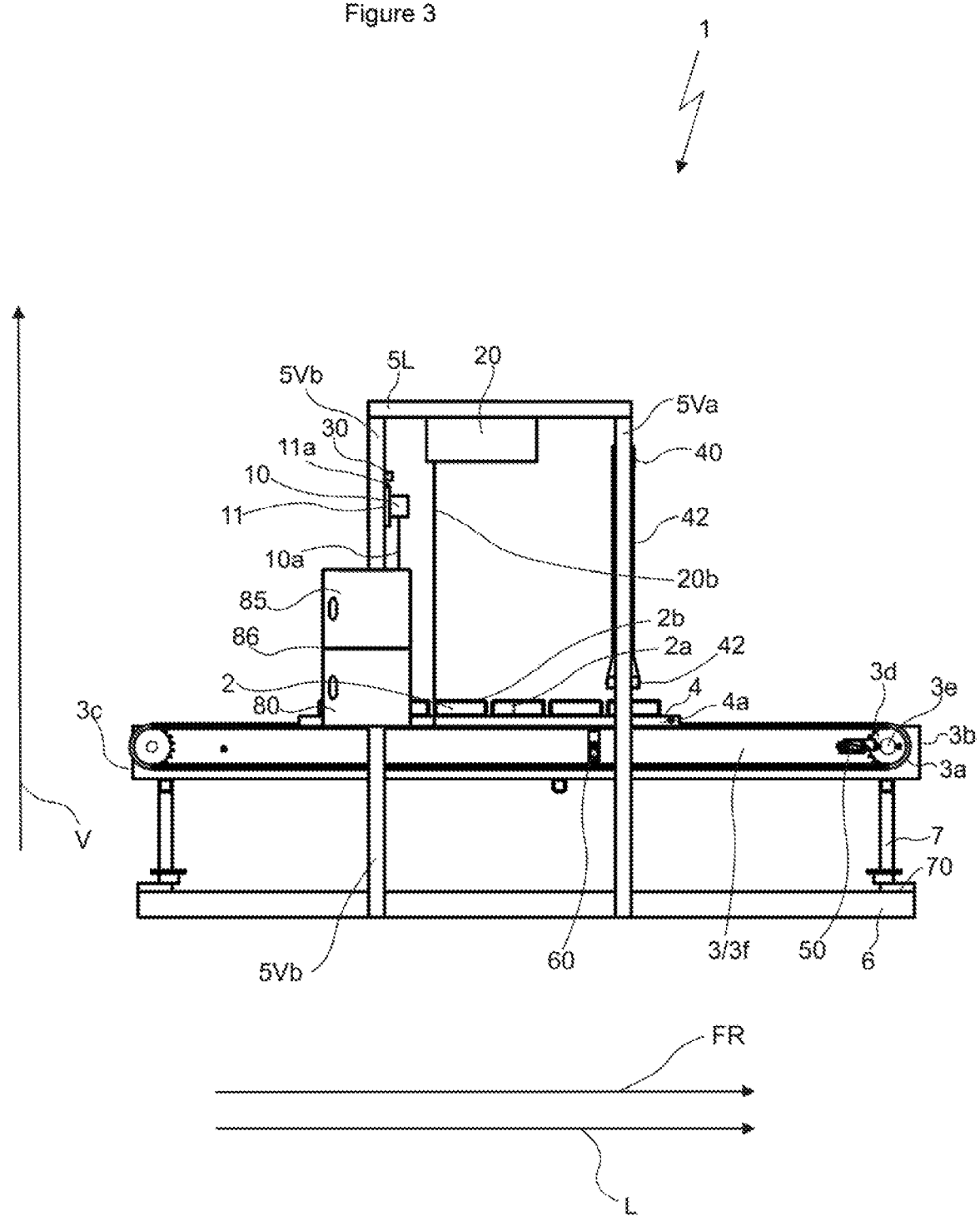

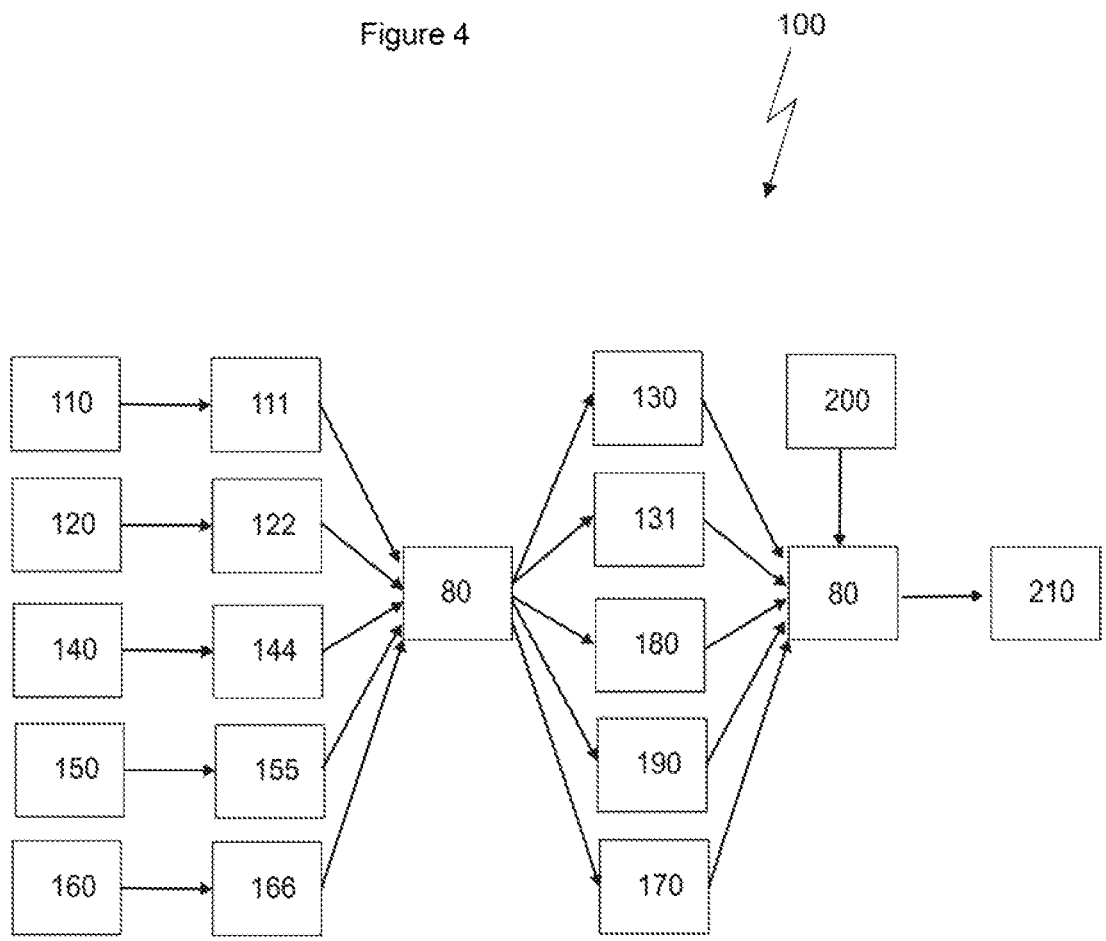

STONE-BLOCK ANALYSIS DEVICE AND METHODS FOR THE EVALUATION OF STONE BLOCKS

The present invention relates to a stone-block analysis device for the evaluation of stone blocks, which comprises at least two scanner units for scanning at least one physical property of the stone blocks. The present invention also relates to a stone-block analysis method for the evaluation of stone blocks and determination of a distance of a conveying surface relative to the upper surface of the stone block located on the conveying surface.

In the production of concrete blocks and other artificially produced stone blocks, or shaped natural stone blocks, it is necessary to check the properties of the stone blocks after processing. In addition to the colouring, the dimensions and surfaces of the stone blocks are of great importance. The concrete blocks are usually produced on a production plate or are placed on such a plate after production. This production plate is then transported with the aid of conveying device systems and guided through a quality monitoring system with the stone blocks on it, which is usually located close behind the production plant. This ensures direct production quality feedback.

In the course of this, the physical properties of the stone blocks are analysed. During the transport of the stone blocks, for example, the height profile of the production plate and the concrete blocks on it is recorded by means of laser sensors. In the case of a surface analysis, the concrete blocks are examined for undesirable elevations and recesses in the surface.

These can form during production, for example, if concrete that is too damp gets stuck on the moulding stamps of the concrete-block moulding machine. Furthermore, the surface structure can be checked for irregularities, which can arise, for example, due to faulty concrete mixtures. Edge spelling can also be detected, which can occur, for example, when concrete blocks deform.

After the production plate has passed through the laser sensor and other sensors, the recorded quality data is evaluated and thus also, for example, the height determination of the concrete blocks. Until now, the height measurement of the stone blocks has been carried out with the aid of laser distance sensors. These sensors measure the distance from the measurement object, i.e. the distance of the stone blocks and the production plate away from the sensor using a laser beam and an integrated light sensor using the triangulation method. For this purpose, only point lasers are usually used.

The problem is that either only a single row of stone blocks can be measured per point laser on the production plate, or the reflected beam, meaning the beam to be measured, is covered in the case of measurement objects that are too high, and therefore cannot be detected or the distance away from the production plate cannot be measured. This problem can also occur with line scanners. In addition, the measurement of the surface of the production plate is particularly difficult if the production plate is uneven, or has damage, for example, in the form of cracks. Such irregularities are particularly difficult to detect or not detectable using point and line scanners if the distance of the measurement objects is so small that the measuring laser beam reaches the surface of the production plate, however, the reflected beam to be detected is covered by measurement objects and thus does not reach the detector. For a better height measurement of many stone blocks on an uneven production plate, therefore, a great number of point lasers are required, which have to be matched to each other and thus incur very high costs. For example, one point laser would have to be used for each row of measurement objects, which would already require 10 point lasers for 10 rows.

SUMMARY OF THE INVENTION

The object of the present invention is therefore to provide a stone-block analysis device, which allows an exact height measurement of the stone blocks to be performed with a low level of technical and financial effort at the same time.

This task is achieved according to which a stone-block analysis device for the evaluation of stone blocks, in particular, concrete blocks, to be arranged on a conveying device for conveying the stone blocks with a conveying surface for the stone blocks to be laid on, which extends in a longitudinal direction and in a transverse direction (which are preferably perpendicular to each other). The stone-block analysis device furthermore comprises at least one first scanner unit for scanning at least one physical characteristic of the stone blocks, an evaluation device for evaluating a signal output by the scanner unit, a control device, and a display device. The scanner unit is spaced away from the conveying surface in a vertical direction, perpendicular to the longitudinal direction and transverse direction.

According to the invention, in addition to the first scanner unit, which comprises a point scanner, at least one second scanner unit is provided, which comprises at least one line scanner, wherein a height of at least one stone block can be detected by both scanner units. Preferably, however, at least two point scanners are provided. By combining at least two point scanners and at least one line scanner, it is possible to detect a conveying surface of the production plate and thus measure the exact height of all stone blocks arranged in a plurality of rows on a production plate.

Preferably, the stone-block analysis device also comprises a frame, on which the scanner units are arranged. This may be a fully enclosed frame, but it is also possible for this frame to have one or a plurality of open areas. Ideally, a transverse profile of the frame extends in the transverse direction and/or is with respect to the vertical direction above the production plate or conveying surface so that the stone blocks are arranged between the transverse profile and the conveying surface. In this case, the transverse profile may also be aligned perpendicularly to the conveying direction or longitudinal direction. Preferably, the first and/or second scanner unit is arranged on the transverse profile of the frame, which extends in the transverse direction, wherein, preferably, the position of the first and/or second scanner unit can be changed in the transverse direction and/or vertical direction, in particular, manually and/or automatically. Preferably, the position of the second scanner unit can be changed in the transverse direction and/or vertical direction and/or longitudinal direction, in particular, manually and/or automatically.

Preferably, the first scanner unit is arranged on a carriage, which is movably and/or height-adjustably arranged on the transverse profile with respect to the vertical direction. Being particularly preferred, the carriage comprises at least one magnet. It is also conceivable that the second scanner unit is arranged below a cover plate and/or on another carriage, which is arranged on the frame in a moveable and/or height-adjustable manner with respect to the vertical direction, in particular, being aligned in parallel with the conveying surface. The position changes can preferably be carried out automatically and thus ensure a precise measurement with different sized stone blocks. The position change is particularly advantageous because it makes a more accurate focusing of the scanner units possible. By being able to change the positions of the scanner units, they can be adjusted to meet the requirements for different production batches.

In a favourable embodiment, the point scanner and/or the line scanner is/are designed as a laser scanner, wherein it is preferably a solid-state laser. However, it is also possible that the laser scanner is a gas laser or a dye laser. Thereby, the point scanner preferably operates at a frequency between 1000 Hz and 15000 Hz, preferably between 2,000 and 10,000 Hz, being particularly preferred, between 2,500 and 7,500 Hz.

The line of the line scanner is preferably generated by an optical lens, which expands a laser beam. In this case, the line preferably extends in the transverse direction across the conveying surface and, in particular, perpendicular to the above-mentioned longitudinal direction.

The line scanner preferably operates at a frequency between 1,000 Hz and 50,000 Hz, preferably between 2,000 and 30,000 Hz, being particularly preferred, between 2,500 and 10,000 Hz. A height profile image of the stone blocks is preferably captured by recording image lines detected by the line scanner. Laser scanners have a particularly high precision in such a way that the stone blocks can be measured precisely. In addition, the size of the laser beams can be adjusted very precisely.

It is further advantageous if the first and/or second scanner unit have at least one light sensor. It is furthermore conceivable that the first and/or second scanner unit comprise a light emitter, which, in particular, is arranged at a measuring angle to a light beam emitted by the light emitter. In this context, the term light can also be understood as electromagnetic radiation. The light beam is preferably vertically directed onto the production plate so that it hits the production plate in a point-shaped or line-shaped manner. The light beam may also be orthogonally aligned with respect to the transverse direction and/or longitudinal direction to enable a particularly precise measurement.

The measuring angle is preferably greater than 20°, preferably greater than 30°, preferably greater than 40° and/or less 80°, preferably smaller than 70°, preferably smaller than 60°, ideally however smaller 90° so that a triangulation measurement method is possible. Thereby, the sensor can be adjusted in such a way that it can detect a beam projected and/or reflected by the light emitter on the conveying surface and/or the stone blocks.

By means of a light sensor, the emitted light or laser beam or the laser beam reflected from the stone block or the conveying surface can be detected. Preferably, the light sensor of the point scanner and/or line scanner is formed as A CCD and/or CMOS sensor. Preferably, the sensor of the line scanner detects between 1,000 and 4,000 points, preferably between 1,000 and 2,000 points, being particularly preferred, between 1,200 and 1,700 points. Depending on the height of the stone blocks and/or the distance of the line scanner away from the stone blocks, a resolution of approx. 1,500 height values per image line can be achieved for the analysis of the stone blocks.

It is favourable if not only the light sensor or a light detection unit of the line scanner is designed as a 3D line scan camera. It is also conceivable that only the light sensor or a light detection unit of the line scanner is designed as a 3D line-scan camera. Preferably, the line scanner is capable of measuring a distance away from a surface of at least one stone block and/or another surface, for example, the surface of the production plate, by means of a triangulation, runtime, and/or light section method.

Preferably, the point scanner is also capable of measuring a distance away from a surface of at least one stone block and/or another surface, for example, the surface of the production plate, by a triangulation, runtime, and/or the light section method. Thus, an absolute distance of the production plate away from at least one scanner unit, as well as the absolute distance of the surface of at least one stone block away from at least one scanner unit can be detected. In addition, it would also be possible to detect a maximum or minimum distance or to determine and/or output an average value.

Preferably, the point scanner is arranged rotated between 40° and 120°, more preferably, rotated between 60 and 100°, being particularly preferred, rotated by 90° with relation to the line scanner. In this case, the line scanner is aligned in the longitudinal direction and/or the point scanner in the transverse direction to a conveying direction. Thereby, it is possible that the light sensors or a viewing direction of the light sensors of the first and second scanner unit or the point and line scanner are arranged at an angle greater than 40°, preferably greater than 60°, preferably greater than 70° and/or less than 120°, preferably less than 110°, preferably smaller than 100°, being particularly preferred, by 90° and/or orthogonally with respect to each other. In this case, the viewing direction of the light sensor of the first scanner unit or the point scanner can be parallel to the transverse direction and/or perpendicular to the longitudinal direction or conveying direction may be aligned.

The viewing direction of the light sensor of the second scanner unit or the 3D line-scan camera can be parallel to the transverse direction or be aligned at least in the longitudinal direction and/or orthogonally with respect to the transverse direction. Such a rotated alignment of the light sensors allows the reflected beam of the point scanner not to be covered by stone blocks moving in the conveying direction, whereby a more precise height measurement of the production plate is made possible. However, the measurement accuracy of the measurement of the stone-block surfaces by the line scanner is increased by an orientation of the light sensor of the line scanner in the conveying direction since the sensor can then detect the laser line along the transverse direction accordingly.

In a further embodiment, the stone-block analysis device comprises at least one detection device for detecting a conveying speed of the conveying surface. Preferably, this is a pulse generator, whereby at least the second scanner unit is controllable. It is conceivable that the pulse generator is designed as an encoder.

The encoder detects positions of a shaft and/or a drive unit and outputs a trigger signal, wherein the positions are optically, magnetically or mechanically detectable. Preferably, the pulse generator triggers the line scanner and/or an image recording device based on the trigger signal. In addition, any acceleration (or deceleration) can also be measured. This has the advantage that the recording of image lines and/or brightness values and/or colour values can be controlled depending on the conveying device.

It is also conceivable that the surface of the stone block can be analysed by the second scanner unit. Preferably, by means of the second scanner unit, a brightness distribution of at least one surface of at least one stone block facing the second scanner unit can be detected. This brightness distribution can be evaluated by the evaluation unit and converted to a grey-value image. By analysing this grey-value image, it is possible to identify spots and/or undesirable deformations of the surface of the stone blocks and to make them visible as a defect by means of the display device and/or to include them in an evaluation of production results.

It is also advantageous if the stone-block analysis device comprises at least one position sensor, by means of which at least one position of the point scanner can be detected with respect to the frame. Preferably, the position sensor is formed as a linear position sensor and/or as a measuring rod, wherein the position sensor detects the position of at least one magnet of a carriage, at which at least one point scanner is arranged. By means of the positions of the point scanners and/or line scanners opposite the frame, the positions of the point scanners and line scanners can also be determined in relation to each other. This allows the positions (or centre points) of the individual stone blocks as well as information about gaps between the stone blocks to be detected.

Preferably, the scanner units, the position sensor and the evaluation unit are data-technically connected via a cable or wirelessly so that data can be exchanged. It is conceivable that the control device is also data-technically connected to the scanner units, the position sensor and/or the evaluation unit. On the basis of this data, the relative height between a surface of the production plate, also between the stone blocks, and the surface of all the stone blocks on the production plate can be detected. Being particularly preferred, the positions of the individual stone blocks detected in this manner can be stored in a database and a curvature of the production plate can be detected. This has the advantage that the actual height of the stone blocks is measurable, wherein the curved surface, caused by the heavy load of stone blocks, of the production plate is taken into account, and defective stone blocks can be sorted out after analysis.

In a preferred embodiment, the stone-block analysis device comprising at least one image recording device, which is suitable and intended for the locally resolved capture of an image. Preferably, the image recording device is designed as a colour camera or a black-and-white camera and/or comprises a CCD sensor, a CMOS sensor and/or another sensor that can detect brightness values and/or colour values. It is conceivable that the image recording device is designed as a line camera and/or individual image lines are captured, which can be combined into an overall image. A colour camera allows for a colour analysis of at least one surface of at least one stone block facing the colour camera to be performed. The colour analysis allows a verification of compliance with specified shades for monochrome surfaces of the stone blocks and/or colour distributions on multi-coloured surfaces of the stone blocks.

Preferably, the stone-block analysis device comprises a lighting device. The lighting device preferably comprises LED lamps, which allow a temporally and colour-constant and uniform illumination for a defined surface section of the conveying surface extending in the transverse direction and/or longitudinal direction. Preferably, a line that can be captured by the image recording device is illuminated by the lighting device. However, it is also conceivable that the lighting system comprises other lamps, for example, a light means based on an incandescent wire and/or mercury vapour. The use of constant and uniform lighting enables the detection of colour patterns of different types of stone block under the same conditions. A deviation of the determined colour patterns from specified colour patterns can thus be optimally detected and evaluated. In addition, hair cracks in stone blocks can be detected by using high-resolution colour cameras and special lighting.

It is advantageous if the stone-block analysis device comprises at least one reading unit, which is suitable for reading a marking. Ideally, a transponder signal or radio tag, a QR code and/or a barcode can be read by the reading unit. If the production plates have an appropriate code or radio tag, this radio tag and/or this code may be detected. As a result, the production plates can be traced with the stone blocks on them. In this way, defective stone blocks can be sorted out via sorting robots after the analysis. It is also possible to measure and/or weigh the production plates once before loading them with stone blocks in order to be able to use the properties of the unloaded production plates in subsequent evaluations.

In a further embodiment, the stone-block analysis device comprises at least one weight measurement unit, whereby a weight of one and/or a plurality of stone blocks on the conveying surface is measurable. Preferably, the weight measurement unit is designed as a load cell. The weight measurement unit can be used to measure the total weight of the production plate and/or the stone blocks on it. Deviations from specified weights can be identified in this way so that incorrectly loaded production plates can be detected at an early stage and/or removed from the conveying device.

It is conceivable that the stone-block analysis device in the standard version comprises at least two and preferably three point scanners and/or two line scanners. In this case, three point lasers may be arranged on the transverse profile, wherein, in particular, a point laser can be arranged as close to one end of the transverse profile with respect to the transverse direction, another point scanner can be arranged as close to another end of the transverse profile as possible, and/or another point scanner can be arranged between the two other to point scanners in the middle with respect to the transverse direction and/or the transverse profile. In this way, height values on the sides of the production plate and a height value in the middle of the production plate can be recorded, so that a curvature of the production plate, which is caused by the loading of the stone blocks, can be taken into account in the determination of the stone block heights.

Furthermore, the frame is preferably made of aluminium, metal, plastic, wood, and/or a composite material. Preferably, the frame comprises a rack made of aluminium profiles and/or strips.

It is also advantageous if the stone-block analysis device comprises a control cabinet that includes the control device and/or evaluation device. In this way, the control device and/or evaluation device are arranged close to each other in such a way that its operation and/or maintenance is facilitated. Preferably, the control device and evaluation device are data-technically connected via a cable or radio communication. Ideally, the analysis of the physical properties of the stone blocks is automated and/or the control device controls the image recording device, the first scanner unit and/or the second scanner unit on the basis of a signal that the evaluation device outputs. Being particularly preferred, the control device also controls a sorting robot, which sorts out flawed stone blocks based on the stored positions of the individual stone blocks.

The task is also achieved by means of a stone-block analysis method for the evaluation of stone blocks, in particular, concrete blocks. The stone-block analysis method is carried out by a stone-block analysis device for arrangement on a conveying device for conveying the stone blocks and with a conveying surface for the stone blocks to be laid on, which extends in a longitudinal direction and a transverse direction (which are preferably perpendicular to each other). The stone-block analysis device furthermore comprises at least one first scanner unit for scanning at least one physical characteristic of the stone blocks, an evaluation device for evaluating a signal output by the scanner unit, a control device, and a display device. The scanner unit is spaced away from the conveying surface in a vertical direction, perpendicular to the longitudinal direction and transverse direction, comprising the steps:
a. detecting a first distance of the first scanner unit to the conveying surface,
b. detecting a second distance of a second scanner unit to an upper surface of a stone block located on the conveying surface,
c. determining a third distance of the conveying surface relative to the upper surface of the stone block located on the conveying surface.

At a first method step, a first distance of the first scanner unit away from the conveying surface is detected, for example, the surface facing the scanner unit of the production plate. Preferably, the first scanner unit transmits a first measurement signal to the evaluation unit. As a result, minor irregularities, such as cracks or dirt on the production plate, can be identified and filtered in the course of later data evaluation and, if necessary, automatically corrected.

A second method step is to detect a second distance of a second scanner unit away from an upper surface of a stone block located on the conveying surface. Preferably, the second scanner unit transmits a second measurement signal to the evaluation unit.

At a third method step, a third distance of the conveying surface relative to the upper surface of the stone block located on the conveying surface is determined. In this way, the exact height of a stone block located on the production plate can be measured.

It is advantageous if, between step b and c, a position of the first scanner unit relative to the second scanner unit is determined and/or specified. This allows the positions of sensors to be measured for distance measurement. It is conceivable that the first scanner unit is formed as a point scanner, which detects the distance of the surfaces of stone blocks to the point scanner and the distance away from the surface facing the scanner unit of the production plate. In this way, gaps between stone blocks, and thus the surface of the production plate between stone blocks, as well as the position of stone blocks on the production plate can be detected. Thus, the number of stone blocks that are arranged on the production plate in a row with respect to the longitudinal direction can also be detected.

Furthermore, it is conceivable that the second scanner unit is formed as a line scanning camera, which, by means of the laser triangulation method, detects an absolute distance of the surface of the stone blocks away from the second scanner unit.

In an embodiment, a, preferably linear, position sensor determines the position of the first to scanner unit opposite the frame and/or transmits a position signal to the evaluation unit. Based on the position signal and the first and/or second measurement signal, the evaluation unit determines the positions of the stone blocks on the production plate, the gaps between the stone blocks and/or the relative distance of the surface of each stone block to the surface of the production plate. In this way, the individual height of each stone block on the production plate is measurable.

It is also conceivable that, on the basis of the first measurement signal and/or a pulse signal, which outputs a pulse generator, a measurement of the second scanner unit and/or an image recording device is controlled.

It is also advantageous if a colour pattern and/or grey-value pattern of the stone blocks is determined via the image recording device, for example, a colour camera, and a colour signal is sent to the evaluation unit. Preferably, the stone blocks are evaluated automatically and/or manually on the basis of the colour signal and specified colour limits.

If the evaluation is positive, the determined colour pattern and/or grey-value pattern is stored, preferably between 100 and 1,000, more preferably between 150 and 800, being particularly preferred, between 250 and 500 colour patterns and/or grey-value patterns. Preferably, stored colour patterns and/or grey-value patterns serve as the basis for evaluations of determined colour patterns and/or grey-value patterns of the stone blocks. As a result, the automatic evaluation is continuously taught. Preferably, therefore, the above-mentioned device comprises a storage device for storing reference data and, in particular, for storing image data.

In one embodiment, a height profile image of the production plate and the stone blocks on it is generated during a transport of the production plate on the basis of the first and/or second measurement signal. Preferably, this height profile image is sent as a signal to the display device and/or displayed as a 3D point cloud in the display device. This allows flawed stone blocks to be made visible and evaluated.

In a further embodiment, a weight of the production plate with stone blocks on it and/or at least one stone block is detected via a weight measurement unit. Preferably, the weight measurement unit sends a weight signal to the evaluation unit.

It is advantageous if the stone blocks are evaluated automatically and/or manually on the basis of the first measurement signal, second measurement signal, position signal, colour pattern, grey-value pattern, weight signal and/or stored parameter. Preferably, a stone-block height is additionally evaluated on the basis of stored parameters, which contain specified information on a set height of the stone block and/or minimum and/or maximum tolerance and/or limit values.

Preferably, a stone-block surface is additionally evaluated on the basis of stored parameters, which contain specified information on tolerance values for a depth and area of a recess and/or height and area of an elevation. Preferably, a stone-block colour is additionally evaluated on the basis of stored parameters, which contain specified information on tolerance values for colour deviations, surfaces of the same or similar colours and/or a ratio of individual colours of a stone block to each other. Preferably, a weight is additionally evaluated on the basis of stored parameters, which contain specified information on tolerance values for the weight of the stone blocks depending on the detected stone block height. Such an evaluation can identify and sort out flawed stone blocks. It is conceivable that the weight of the stone blocks is decisive for such an evaluation.

In a further embodiment, the determined weight of the empty production plate, the production plate with stone blocks on it and/or at least one stone block, the determined stone-block height, the determined height profile image, the determined colour pattern, the determined grey-value pattern, a position of a stone block on the production plate and/or a marking of the production plate are stored in a database. Preferably, a weight of an empty production plate with a marking of the same production plate coupled is stored in the database. This makes it possible to determine an empty weight of a production plate loaded with stone blocks and to deduct this empty weight from the weight of a production plate loaded with stone blocks and thus to determine a weight of the stone blocks. However, it is also conceivable that an average weight of a plurality of empty production plates is stored manually in the database via the control device.

Other objectives, advantages, features and application possibilities of the present invention result from the following description of exemplary embodiments based on the figures. Thereby, all described and/or graphically represented features form the object of the invention on their own or in any sensible combination.

BRIEF DESCRIPTION OF THE DRAWINGS

The figures show:

FIG. 3 a schematic lateral view of a stone-block analysis device

FIG. 4 schematic presentation of a method for the evaluation of stone blocks

DETAILED DESCRIPTION OF THE INVENTION

Figure 1:
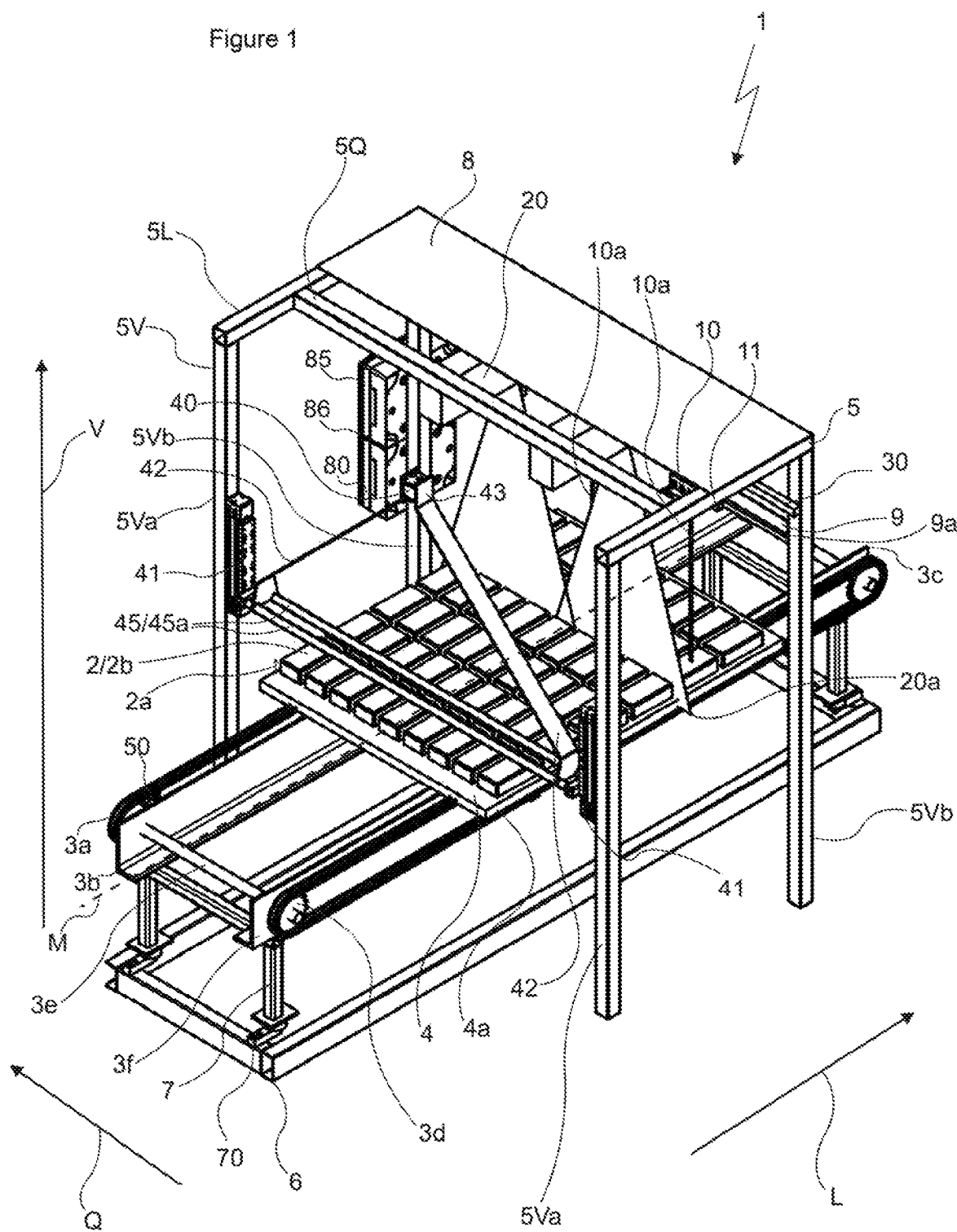
FIG. 1 a schematic perspective view of a stone-block analysis device

FIG. 1 shows a conveying device 3 and a stone-block analysis device 1. The stone-block analysis device 1 comprises a frame 5 and at least one first scanner unit 10. The stone-block analysis device 1 is modular so that individual elements, in particular, scanners and/or sensors, are arranged in a moveable manner with respect to the frame 5. It is also possible to spend additional elements, in particular, scanners and/or sensors, retrospectively on the frame 5, or to extend the frame with additional frame elements. In this way, the stone-block analysis device 1 can be adapted to the intended application as desired.

The conveying device 3 comprises a base 6 and at least one chain conveyor, but, preferably, two chain conveyor 3a, which can be moved in the longitudinal direction L so that a conveying element 4a with a conveying surface 4 can be transported in the longitudinal direction L by the chain conveyors 3a via the conveying device. A pulse generator 50 and/or a weight measurement unit 70 of the stone-block analysis device 1 are arranged on the conveying device 3.

The chain conveyors 3a extend in the longitudinal direction L from a rear end 3b to a front end 3c of the conveying device 3. Preferably, the chain conveyors 3a are driven by toothed gears 3d, which are laterally arranged on the conveying device 3 and parallel to a lateral surface 3f extending in the vertical direction V and the transverse direction Q. At one end 3b, 3c, the conveying device 3 are arranged at least two toothed gears, which are connected by a rotatable axis 3e. At least one pulse generator 50 is arranged on a toothed gear and/or the to rotatable axis. The conveying device 3 contacts the base 6 by means of support elements 7. Preferably, between the base 6 and the support elements 7, at least one weight measurement unit 70 is arranged between the support elements 7 and the conveying device 3 and/or between the conveying device 3 and the conveying element 4a.

The frame 5 comprises vertical elements 5V, longitudinal elements 5L, transverse elements 5Q and/or a cover plate 8, which extends a longitudinal direction L and transverse direction Q. Preferably, laterally arranged coverings (not drawn in) are also arranged on the vertical elements 5V, which extend in the longitudinal L and vertical direction V. Preferably, a front vertical element 5Va and a rear vertical element 5Vb is arranged at the ends of a longitudinal element 5L and each two longitudinal elements 5L at ends of each of two transverse elements 5Q. The cover plate is arranged on at least two longitudinal elements 5L and at least one transverse element 5Q. The conveying device 3 is arranged between the two front vertical elements 5Va and the two rear vertical elements 5Vb, wherein the front vertical elements 5Va and rear vertical elements 5Vb are each so spaced away from each other in such a way that a conveying element 4a with a preferred width with respect to the transverse direction Q between 100 cm and 300 cm, more preferably between 120 cm and 150 cm, can be transported by the conveying device 3.

Two height adjustment devices 41 are arranged on the two front vertical elements 5Va, which are opposite to each other, wherein the height adjustment devices 41 are arranged in the vertical direction V above the conveying device 3 and above the conveying surface 4. The lighting device 45 extends between the two height adjustment devices 41 and their height with respect to the vertical direction V can be changed by the height adjustment devices 41. In this case, at least two retaining elements 42 are arranged on the lighting device 45 and/or a height adjustment devices 41 respectively, at the upper ends 43 of which the image recording device 40 is transported. In this case, the height of image recording device 40 can be changed with respect to the vertical direction V dependent on or independent from the lighting device 45 by means of the height adjustment devices 41.

The lighting device 45 comprises two illumination elements 45a, which extend in the transverse direction and are distanced away from each other with respect to the longitudinal direction L. Furthermore, the illumination elements 45a are aligned parallel to the conveying surface 4, wherein the image recording device 40 is aligned in such a way that it captures an image of a section of the conveying surface 4 between the two illumination elements 45a.

Between the two rear vertical elements 5Vb a transverse profile 9 is arranged, which extends in the transverse direction Q and comprises at least one groove running in the transverse direction Q. On the groove 9a, at least one carriage 11 is arranged, which can be moved in the transverse direction. The carriage 11 comprises at least one first scanner unit 10 and one magnet. Parallel to the transverse profile, a position sensor is arranged, which is preferably bar-shaped. The position sensor 30 also extends in the transverse direction Q and is moved between the two rear vertical elements 5Vb and/or above the transverse profile 9 and/or above the first scanner unit 10. In addition, the position sensor 30 is able to detect the magnet of the carriage 11 and, in this way, it able to detect the position of the first scanner unit 10 relative to the frame 5.

Preferably, the stone-block analysis device 1 comprises three first scanner units 10, which are designed as point scanners 10. The three point scanners 10 are each arranged on a carriage with one magnet. Each a point scanner 10 is aligned in such a way that a point scanner 10 with respect to the vertical direction V and transverse direction Q is arranged above each a chain conveyor 3a and a laser beam 10a perpendicular to the longitudinal direction L and transverse direction Q hits the conveying surface 4. The third point scanner 10 is aligned in such a way that the laser beam 10a preferably hits the conveying surface 4 at a centre line M perpendicularly with respect to the longitudinal direction L and transverse direction Q. Preferably, the point scanners are arranged between 10 cm and 150 cm above the conveying surface 4, more preferably, between 30 cm and 100 cm above the conveying surface 4, being particularly preferred arranged between 50 cm and 80 cm above the conveying surface 4, with respect to the vertical direction V.

Preferably, the stone-block analysis device 1 comprises two second scanner units 20, which are designed as line scanners 20, preferably as a laser line scanners. Thereby, the laser beam 20b emitted by the line scanner extends with respect to the transverse direction Q and/or spreads out in a fan-like manner and hits the conveying surface 4 and/or the surface 2b of the stone blocks 2. The scan line 20a is aligned parallel to the transverse direction Q and perpendicular to the longitudinal direction L and vertical direction V. Preferably, the line scanners 20 are arranged between 20 cm and 200 cm above the conveying surface 4, more preferably, between 50 cm and 150 cm above the conveying surface 4, being particularly preferred, arranged between 65 cm and 100 cm above the conveying surface 4 with respect to the vertical direction V. Ideally, the line scanners 20 are arranged on and/or at least one transverse element 5Q.

A control cabinet is arranged on a vertical element 5V, a transverse element 5Q and/or a longitudinal element. The control cabinet 86 comprises an evaluation device 80 and/or a control device 85.

Figure 2:
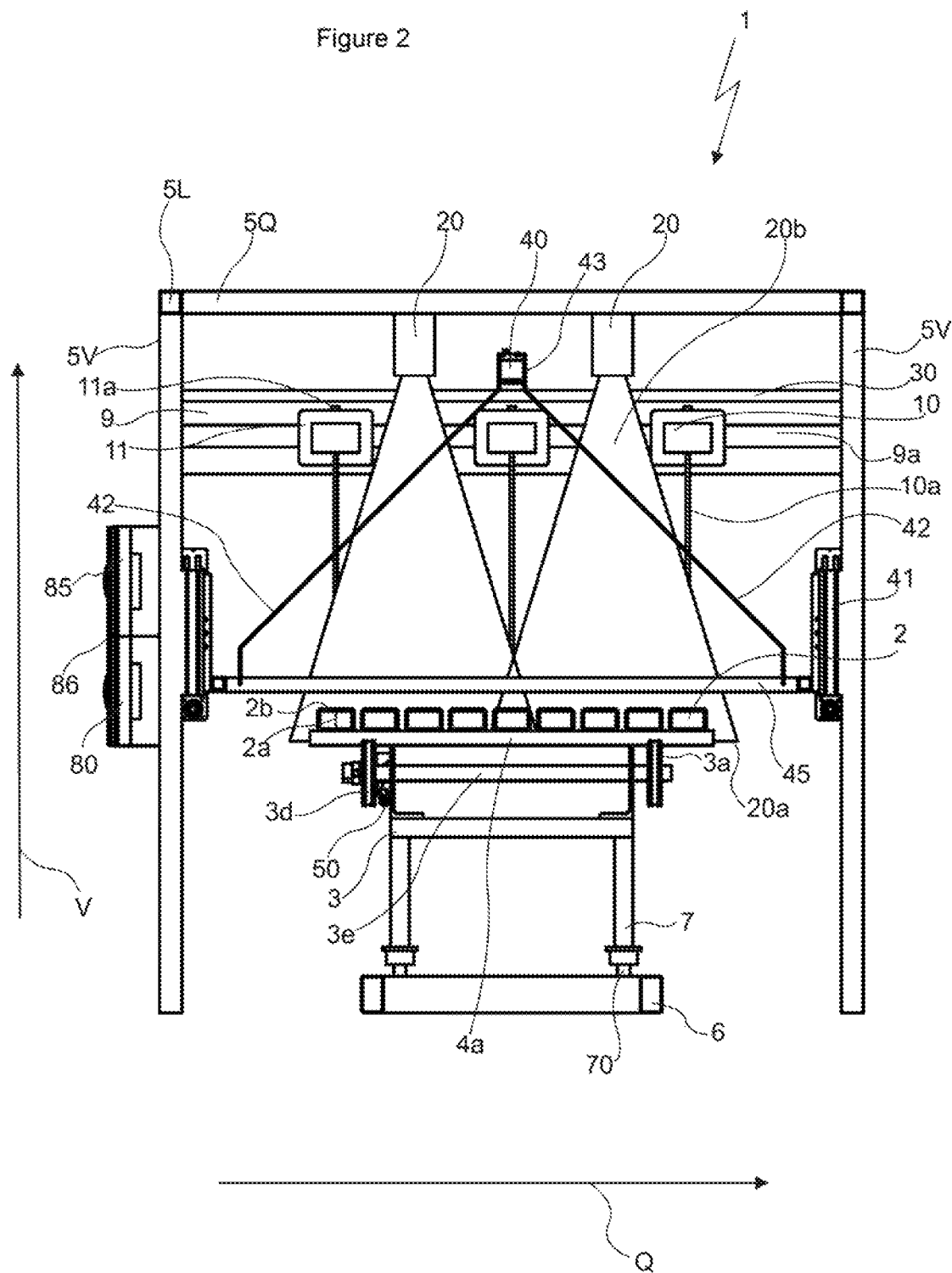
FIG. 2 a schematic front view of a stone-block analysis device

In FIG. 2, the stone-block analysis device 1 is shown in a front view. The three point scanners 10 are arranged at the moveable carriages 11 with the magnets 11a at the groove 9a of the transverse profile 9. Thereby, with respect to the transverse direction Q, the point scanners 10 are arranged next to one another, being arranged spaced away from one another. The position sensor 30 is arranged parallel to the transverse profile 9. Regarding the vertical direction V, the line scanners 20 are arranged at a greater distance away from the conveying surface 4 than the point scanners 10. The conveying surface with the stone blocks 2 on it is arranged with respect to the vertical direction V below the point scanner 10, the line scanner 20, the lighting device 45 and/or the image recording device 40. Thus, the height of the stone blocks 2a can be optimally measured by the point scanners 10 and/or the line scanners 20.

In FIG. 3, the stone-block analysis device 1 is shown in a lateral view. The conveying element 4a with the stone blocks 2 on it is transported in the conveying direction FR via the conveying device 3 and the chain conveyors. With respect to the longitudinal direction L, the measurement devices are arranged one after the other so that the pulse generator 50 is arranged at the rear end 3b of the conveying device 3. The lighting device 45 and the image recording device 40 are arranged closer to the rear end 3b than at the front end 3c. With respect to the longitudinal direction L, the point scanners 10 are arranged closer to the front end 3c than at the rear end 3b. With respect to the longitudinal direction L, the line scanners 20 are arranged between the point scanners 10 and the image recording device 40. Thereby, a reading unit is arranged on the conveying device 3 below the conveying element 4a with respect to the vertical direction V and/or with reference to longitudinal direction L, preferably between the rear end 3b and the lighting device 45, or between the lighting device 45 and the line scanner 20 and/or the point scanner 10.

FIG. 4 shows a stone-block analysis method 100 for the evaluation of 210 of stone blocks 2.

At a first method step, a first distance 110 of the first scanner unit 10 to the conveying surface 4 is detected. Preferably, the first scanner unit 10 transmits a first measurement signal 111 to the evaluation unit 80 on the basis of the first distance 110.

A second method step entails detecting a second distance 120 of a second scanner unit 20 away from an upper surface 2b of a stone block 2 located on the conveying surface 4. Preferably, the second scanner unit 20 transmits a second measurement signal 122 to the evaluation unit 80 on the basis of the second distance 120.

An advantageous method step provides that a position 140 of a magnet of a carriage is detected by the position sensor 30, on which the first scanner unit is arranged, meaning detecting a position 140 of the first scanner unit 10 with relation to the frame 5. Preferably, the position sensor 30 transmits a position signal 144 to the evaluation unit 80 on the basis of the position 140.

An advantageous method step provides that, via the image recording device 40, a colour pattern 150 of the stone blocks is determined and, on the basis of which a colour signal 155 is sent to the evaluation unit 80.

Preferably, a weight 160 of the conveying element 4a with stone blocks 2 on it is also determined and, on the bases of this, a weight signal 166 is sent by the weight measurement unit 70 to the evaluation unit 80.

At another method step, the first measurement signal 111, the second measurement signal 122, the position signal 144, the colour signal 155 and/or weight signal 166 in the evaluation unit 80 are evaluated. On the basis of the first measurement signal 111, the second measurement signal 122, the position signal 144, the colour signal 155 and/or weight signal 166, a stone-block height 2a or a third distance 130 of the conveying surface 4 relative to the upper surface 2b of the stone block 2 located on the conveying surface 4, an height profile image 131, a stone-block surface 170, a stone-block colour 180 and/or a stone-block weight 130 are determined.

After determining the characteristics of the stone blocks 2, stored parameters 200 are used to evaluate 210 the stone blocks 2. Preferably, the stored parameters have 200 default values, which, together with the stone-block height 2a, the height profile image 131, the stone-block surface 170, the stone-block colour 180 and/or the stone-block weight 130 form a basis for the evaluation 210. Preferably, the default values or stored parameters 200 comprise information on tolerance values for a depth and area of a recess and/or height and area of an increase of a stone-block surface, as well as information on tolerance values for colour deviations, surfaces of the same or similar colours and/or a ratio of individual colours of a stone block to each other, as well as information on tolerance values for a stone-block weight 190 depending on the determined stone-block height 2a.

The applicant reserves the right to claim all the features disclosed in the application documents as crucial to the invention, provided that they are new with relation to prior art individually or in combination. It is furthermore noted that, in the individual figures, features were also described, which may be advantageous in themselves. The person skilled in the art immediately recognizes that a particular feature described in a figure may be advantageous even without the adoption of further features from that figure. Furthermore, the person skilled in the art recognizes that advantages may also arise from a combination of a plurality of features shown in individual or different figures.

REFERENCE LIST 1. stone-block analysis device
2. stone block/stone blocks
2a. height of a stone block
2b. surface of a stone block
3. conveying device
3a. chain conveyors
3b. rear end
3c. front end 3d. toothed gears
3e. rotatable axis
3f. lateral area
4. conveying surface
4a. conveying element
5. frame
5L. longitudinal elements
5Q. transverse elements
5V. vertical elements
5Va. front vertical elements
5Vb. rear vertical elements
6. base
7. support elements
8. cover plate
9. transverse profile
9a. groove
10. first scanner unit/point scanner
10a. laser beam
11. carriage
11a. magnet
20. second scanner unit/line scanner
20a. scan line
20b. laser beam of the line scanner
30. position sensor
40. image recording device
41. height adjustment device
42. retaining elements
43. upper end
45. lighting device
45a. illumination element
50. pulse generator/encoder
60. reading unit
70. weight measurement unit
80. evaluation device
85. control device
86. control cabinet
100. stone-block analysis method
110. first distance
111. first measurement signal
120. second distance
122. second measurement signal
130. third distance
131. height profile image
140. positions of the first scanner unit
144. position signal
150. colour pattern
155. colour signal
160. weight
166. weight signal
170. stone-block surface
180. stone-block colour
190. stone-block weight
200. stored parameters
210. evaluation
L. longitudinal direction
Q. transverse direction
V. vertical direction
FR. conveying direction
M. centre line

The invention claimed is:

1. A stone-block analysis device for the evaluation of stone blocks, comprising a conveying device for conveying the stone blocks with a conveying surface for the stone blocks to be laid on, which extends into a longitudinal direction (L) and into a transverse direction (Q), wherein the stone-block analysis device comprises at least a first scanner unit configured for scanning at least one physical characteristic of the stone blocks, an evaluation device configured for evaluating a signal output by the scanner unit, a control device, and a display device, wherein the scanner unit is spaced away from the conveying surface in a vertical direction (V), perpendicular to the longitudinal direction (L) and transverse direction (Q),
wherein
in addition to the first scanner unit, which comprises a point scanner, at least one second scanner unit which comprises at least one line scanner is provided, wherein a height of the at least one stone block can be detected by both scanner units, wherein the line of the line scanner is generated by an optical lens, which expands a laser beam to a line, wherein the expanded line extends in the transverse direction across the conveying surface and perpendicular to the longitudinal direction, wherein the second scanner unit is confirmed to analyze, the surface of the stone block.

2. The stone-block analysis device according to claim 1, wherein
the first scanner unit and/or the second scanner unit comprises a laser scanner.

3. The stone-block analysis device according to claim 1, wherein
the first scanner unit and/or the second scanner unit comprise at least one light sensor.

4. The stone-block analysis device according to claim 3, wherein
a viewing direction of the light sensors of the first scanner unit and the second scanner unit is at an angle selected from the group consisting of greater than 40°, prcfcrably greater than 60°, prcfcrably greater than 70° and/or less than 120°, prcfcrably less than 110°, prcfcrably smaller less than 100°, being particularly preferred, by less than 90° and/or orthogonally arranged with respect to each other.

5. The stone-block analysis device according to claim 3, wherein
the viewing direction of the light sensor of the first scanner unit is aligned parallel to the transverse direction (Q) and/or perpendicular to the longitudinal direction (L).

6. The stone-block analysis device according to claim 3, wherein
the viewing direction of the light sensor of the second scanner unit is aligned in the longitudinal direction (L) and/or orthogonally with respect to the transverse direction (Q).

7. The stone-block analysis device according to claim 1, wherein
the stone-block analysis device comprises first second and third point scanners, wherein the first point scanner is arranged between the second and third point scanners in the centre with respect to the transverse direction (Q).

8. The stone-block analysis device according to claim 1, wherein
the stone-block analysis device comprises at least one speed detection device and, in particular, at least one pulse generator, whereby at least the second scanner unit is controllable.

9. The stone-block analysis device according to claim 1, wherein
the stone-block analysis device comprises at least one position sensor configured to detect a position of the point scanner with respect to a frame.

10. The stone-block analysis device according to claim 1, wherein
the stone-block analysis device comprises at least one image recording device, which is configured for the locally resolved capture of an image and/or comprises a lighting device.

11. The stone-block analysis device according to claim 1, wherein
the stone-block analysis device comprises at least one reading unit configured for reading a marking.

12. The stone-block analysis device according to claim 1, wherein
the stone-block analysis device comprises at least one weight measurement unit configured for measuring a weight of one and/or a plurality of stone blocks on the conveying surface.

13. A stone-block analysis method for the evaluation of stone blocks, using a stone-block analysis device for arrangement on a conveying device for conveying the stone blocks with a conveying surface for the stone blocks to be laid on, which extends into a longitudinal direction (L) and into a transverse device (Q), wherein the stone-block analysis device comprises at least one first scanner unit configured for scanning at least one physical characteristic of the stone blocks, an evaluation device configured for the evaluation of a signal output by the scanner unit, a control device, and a display device, wherein the scanner unit is spaced away from the conveying surface in a vertical direction (V), perpendicular to the longitudinal direction (L) and transverse direction (Q), wherein in addition to the first scanner unit, which comprises a point scanner, at least one second scanner unit which comprises at least one line scanner is provided, wherein a height of the at least one stone block can be detected by both scanner units, wherein the line of the line scanner is generated by an optical lens, which expands a laser beam to a line , wherein the expanded line extends in the transverse direction across the conveying surface and perpendicular to the longitudinal direction, said method comprising the steps:
a. detecting a first distance of the first scanner unit to the conveying surface,
b. detecting a second distance of a second scanner unit to an upper surface of a stone block located on the conveying surface,
c. determining a third distance of the conveying surface relative to the upper surface of the stone block located on the conveying surface.

14. The stone-block analysis method according to claim 13, wherein
a position of the first scanner unit relative to the second scanner unit is determined and/or specified.

15. The stone-block analysis device according to claim 2, wherein
the first scanner unit and/or the second scanner unit comprise at least one light sensor.

16. The stone-block analysis device according to claim 15, wherein
a viewing direction of the light sensors of the first scanner unit and the second scanner unit is at an angle selected from the group consisting of greater than 40°, greater than 60°, prcfcrably greater than 70° and/or less than 120°, prcfrably less than 110°, less than 100°, less than 90° and/or orthogonally arranged with respect to each other.

17. The stone-block analysis device according to claim 15, wherein
the viewing direction of the light sensor of the first scanner unit is aligned parallel to the transverse direction (Q) and/or perpendicular to the longitudinal direction (L).

18. The stone-block analysis device according to claim 15, wherein
the viewing direction of the light sensor of the second scanner unit is aligned in the longitudinal direction (L) and/or orthogonally with respect to the transverse direction (Q).

19. The stone-block analysis device according to claim 7, wherein
the stone-block analysis device comprises at least one position sensor configured to detect a position of the point scanner with respect to a frame.

* * * * *